(12) United States Patent
Haase

(10) Patent No.: US 6,293,922 B1
(45) Date of Patent: Sep. 25, 2001

(54) APPARATUS AND METHOD FOR GUIDING AND LIMITING ACCESS BY HYPODERMIC NEEDLES TO SEPTUM OF A HUMAN IMPLANTABLE MEDICAL TREATMENT DEVICE

(75) Inventor: James Martin Haase, Maplewood, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/561,528

(22) Filed: Apr. 28, 2000

(51) Int. Cl.$^7$ .................................................. A61M 11/00
(52) U.S. Cl. .............................................................. 604/93
(58) Field of Search ........................ 604/93, 175, 164.01, 604/117, 116

(56) References Cited

U.S. PATENT DOCUMENTS

| 4,573,994 | 3/1986 | Fischell et al. . |
| 4,576,556 | 3/1986 | Thompson . |
| 5,328,465 | 7/1994 | Kratoska et al. . |
| 5,711,316 | 1/1998 | Elsberry et al. . |

*Primary Examiner*—Manuel Mendez
(74) *Attorney, Agent, or Firm*—Banner & Witcoff, Ltd.

(57) ABSTRACT

A conical depression for guiding a hypodermic needle into a desired location and having a hole at the center for limiting the maximum needle diameter that can be used to access that location. The diameter of the hole prevents access by needles having a diameter greater than the diameter of the hole. The conical depression has a smooth surface and an angle such that needles that are inserted into the conical depression misaligned with the hole will be guided to the hole without damaging the tip of the hypodermic needle.

7 Claims, 5 Drawing Sheets

APPARATUS AND METHOD FOR GUIDING AND LIMITING ACCESS BY HYPODERMIC NEEDLES TO SEPTUM OF A HUMAN IMPLANTABLE MEDICAL TREATMENT DEVICE

TECHNICAL FIELD

This invention relates generally to apparatus and methods for limiting access by hypodermic needles to a septum of a human implantable medical treatment device. More particularly, the invention is directed to a simplified, less expensive method and apparatus involving a conical depression for guiding misaligned hypodermic needles and a hole at the center of the depression for limiting access to the septum to hypodermic needles having a diameter no greater than a predetermined size.

BACKGROUND OF THE INVENTION

Medicament pumps, such as, the peristaltic pump disclosed in commonly assigned U.S. Pat. No. 4,576,556, which is incorporated herein by reference, are well known in the prior art and have wide application in the medical field. A typical application for such a pump is implanting the pump within a patient's body for treating a neurodegenerative disease or trauma, as is disclosed in commonly assigned U.S. Pat. No. 5,711,316, which is incorporated herein by reference. Other applications are also well known. The term "medicament pump" as used herein, refers to any device for delivering medicaments including, but not limited to, bladder pumps, accumulator pumps, fixed-rate bellows pumps, and the like.

Implantable devices, such as medicament pumps, are in frequent use for delivering drugs or other liquid medications over long periods of time to selected locations in the human body. These devices commonly include a drug reservoir, catheter means connected to the reservoir to transport the drug and a pumping mechanism to propel the drug in some metered or constant flow dosage to the desired location. Over time, the drug in the reservoir becomes depleted and it is necessary to refill the device with a new supply of drug. In order to avoid the need for surgery in order to access and refill the device, it is desirable to have the ability to refill the drug reservoir percutaneously. This is commonly done by providing the medicament pump with a resilient resealable reservoir fill port septum which is accessible by injecting a hypodermic needle through the skin and into the septum thereby providing access to refill the reservoir.

In such devices a catheter access port septum is often provided in addition to the reservoir fill port septum. The catheter access port septum is also accessible percutaneously by hypodermic needle. This septum provides direct access to the catheter bypassing the pump and allows a bolus of drug or fluid medication to be administered directly into the body at the site of the catheter.

Although providing a catheter access port septum is both desirable and advantageous a problem can develop if the person refilling the reservoir incorrectly injects the drug into the catheter access port septum instead of the reservoir fill port septum. This results in the drug being administered directly to the body. This may potentially cause an overdose of drug or other serious problems because the pump should administer the drug over a period of time.

This problem has been addressed previously. For instance, U.S. Pat. No. 5,328,465, issued to Kratoska et al. on Jul. 12, 1994, which is incorporated herein by reference, discloses a screen for covering a medicament pump catheter access port. The screen limits access to the catheter access port septum to hypodermic needles smaller than a predetermined size. A few shortcomings of such screens are that they tend to damage hypodermic needles when a needle is inserted not aligned with a hole in the screen. Such screens are also relatively expensive and difficult to manufacture.

U.S. Pat. No. 4,573,994 issued to the Fischell et al. on Mar. 4, 1986, discloses a conical depression as part of a system and method for accessing a medicament pump reservoir access port. Fischell et al., however, does not disclose limiting access to a port by hypodermic needles smaller than a predetermined size.

Accordingly, a need exists for a simplified, less expensive device and method that eliminates, or at least reduces the possibility of, inadvertent injections of drug directly into the catheter access port without damaging hypodermic needles.

SUMMARY OF THE INVENTION

According to various preferred embodiments, the invention includes apparatus and methods wherein: a conical depression having a hole at the center guides a hypodermic needle into a desired location, such as the catheter access port septum of a human implantable medicament pump. The diameter of the hole prevents access to the location by needles having a diameter greater than the diameter of the hole. The conical depression has a smooth surface and an angle such that needles that are inserted into the conical depression misaligned with the hole will be guided to the hole without damaging the tip of the hypodermic needle. This is simpler than, less expensive than, and unlike conventional screens for limiting access to a septum, which screens tend to damage the tips of misaligned hypodermic needles.

Other features and advantages of the invention will become apparent through the following description, the figures, and the appended claims.

DETAILED DESCRIPTION OF THE INVENTION

Figure 1:
FIG. 1 is a diagrammatic illustration of a medicament pump coupled to a catheter that is implanted in the brain of a patient.

Referring to FIG. 1, a medicament pump, also referred to as a device, 10 may be implanted below the skin of a patient. The device has a reservoir access port 14 into which a hypodermic needle can be inserted through the skin to inject a quantity of a liquid agent, such as a medication or drug. The liquid agent is delivered from device 10 through an outlet port 20 into a catheter 22. Catheter 22 may be positioned to deliver the agent to specific infusion sites in brain (B) or other appropriate locations within a person's body.

Figure 2:
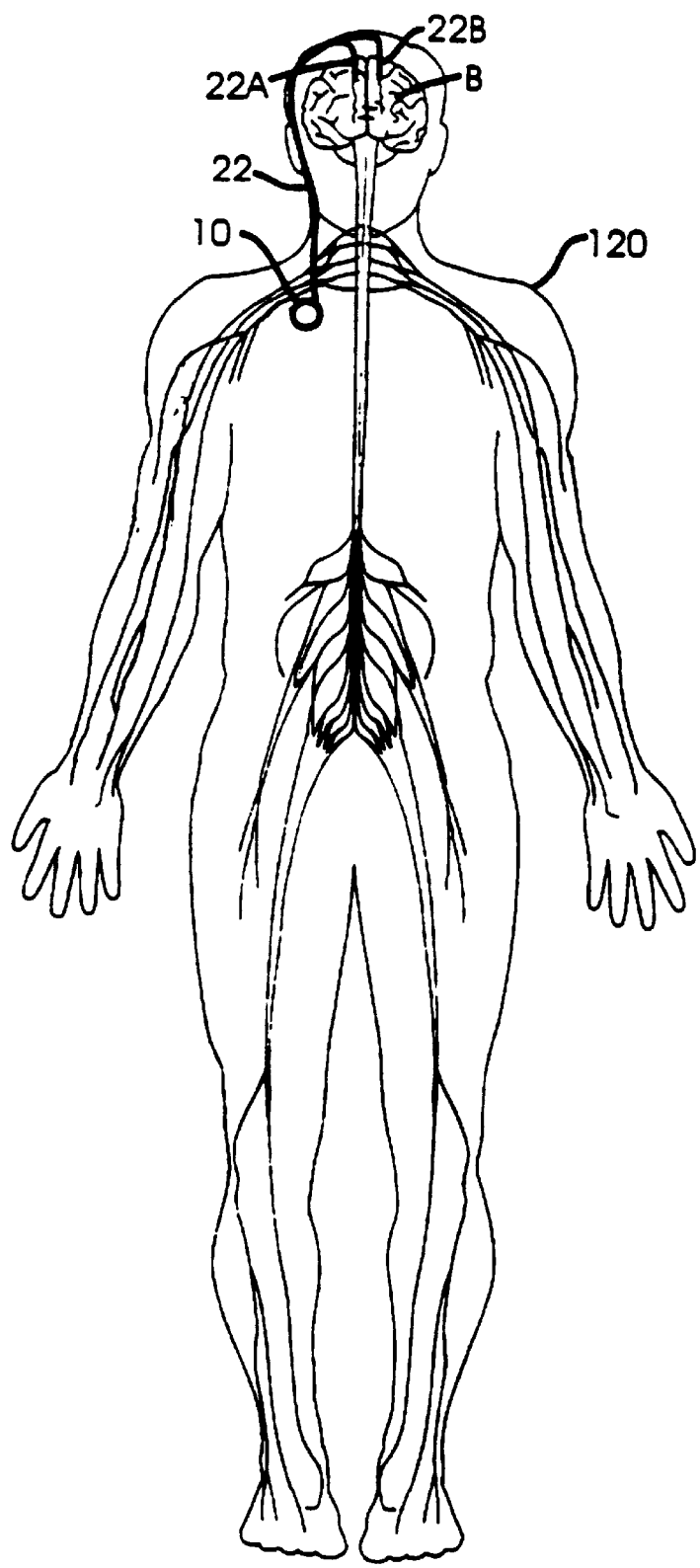
FIG. 2 is a diagrammatic illustration of a portion of the nervous system of a human body in which a medicament pump and catheter have been implanted.

Referring to FIG. 2, device 10 is implanted to a human body 120 in the location shown. Alternatively, device 10 may be implanted in the abdomen. Catheter 22 may be divided into twin tubes 22A and 22B that are implanted into the brain bilaterally.

Figure 3:
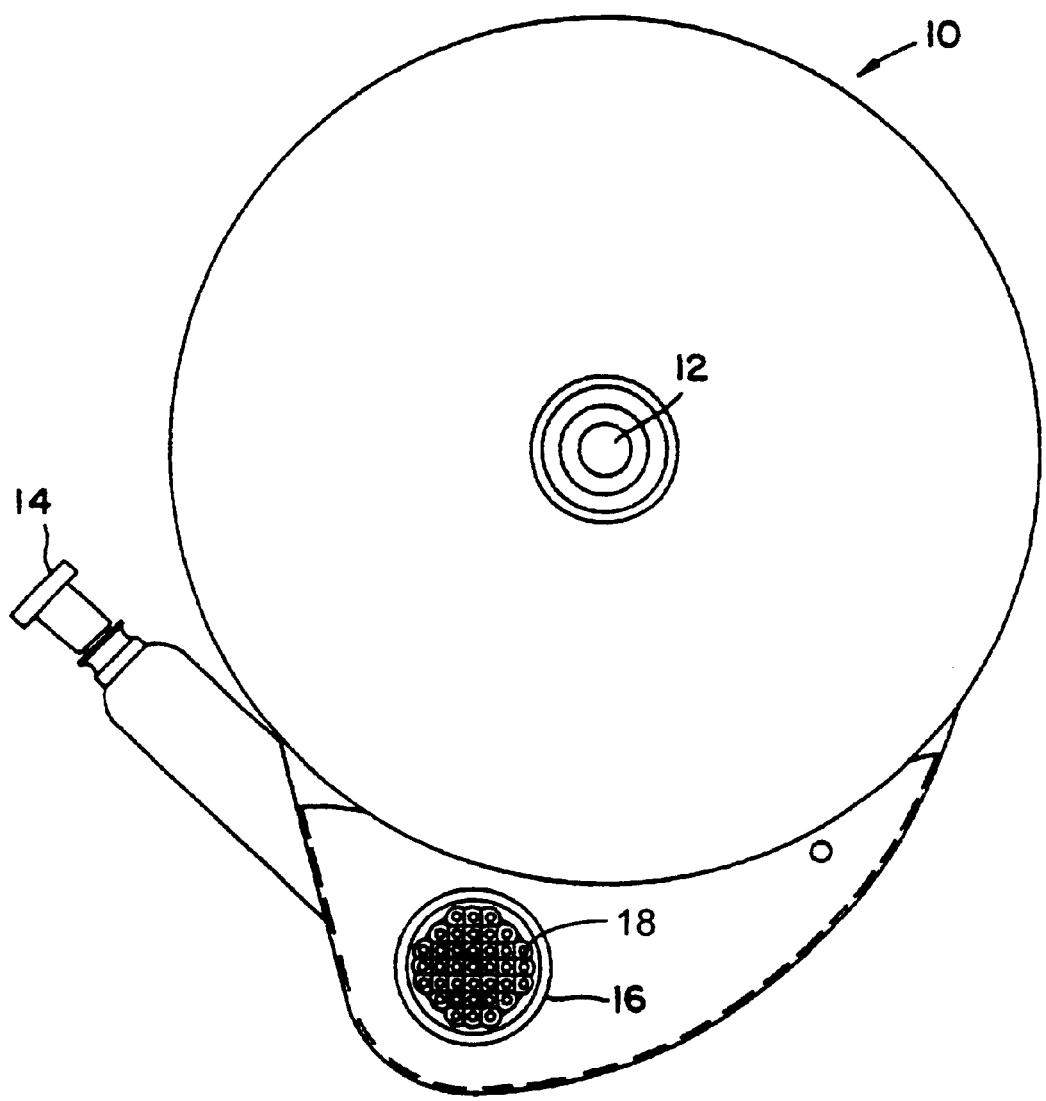
FIG. 3 is a top view of a schematic illustration of a medicament pump having a prior art screen for limiting access to a catheter access port septum.

Referring to FIG. 3, a medicament pump having a screen for limiting catheter port access to hypodermic needles smaller than a predetermined size, such as the screen disclosed in U.S. Pat. No. 5,328,465, issued to Kratoska et al. on Jul. 12, 1994, is shown. As previously mentioned, such screens disadvantageously tend to damage hypodermic needles when a needle is inserted not aligned with a hole in the screen. Such screens are also relatively expensive and difficult to manufacture.

FIG. 3 is a top view of a body implantable medicament pump 10 incorporating a screen, such as disclosed by Kratoska et al. Pump 10 includes a reservoir fill port septum 12, which is percutaneously accessible by a hypodermic needle. Fill port septum 12 is comprised of a resilient, resealable material such as silicone rubber, which is durable enough to withstand numerous punctures without leaking. A reservoir (not shown) may be filled by inserting a needle through the skin into fill port septum 12 and injecting the drug into the reservoir. Drug pump 10 is of conventional design known in the art such as the SynchroMed® Infusion System manufactured by Medtronic, Inc. of Minneapolis, Minn.

Medicament pump 10 further includes a catheter access port 16. Catheter access port 16 provides direct percutaneous access via a hypodermic needle to catheter outlet port 14. This allows the direct injection through access port 16 of a bolus of medication or drug to the site of the catheter without going through the pump 10. As depicted in FIG. 3, a screen 18, comprising a plurality of holes, covers catheter access port 16.

The openings in screen 18 are sized to prohibit access to the septum of catheter access port 16 by a needle in excess of a certain size or gauge. For example, a refill kit for the SynchroMed® pump includes a 22 gauge needle. Thus, in order to prevent the inadvertent insertion of the refill needle into the catheter access port septum, the openings are sized so that a 22 gauge needle will not pass through the screen. Therefore, the septum can not be punctured and the possibility of inadvertent injection directly into the body through the catheter access port septum is virtually eliminated. Should direct injection of a bolus of medication or drug through the catheter access port septum be desired a smaller needle, for example, a 25 gauge needle, can be used. The holes of screen 18 are sized so that access is permitted to a 25 gauge needle, but prohibited to the 22 gauge needle.

Figure 4:
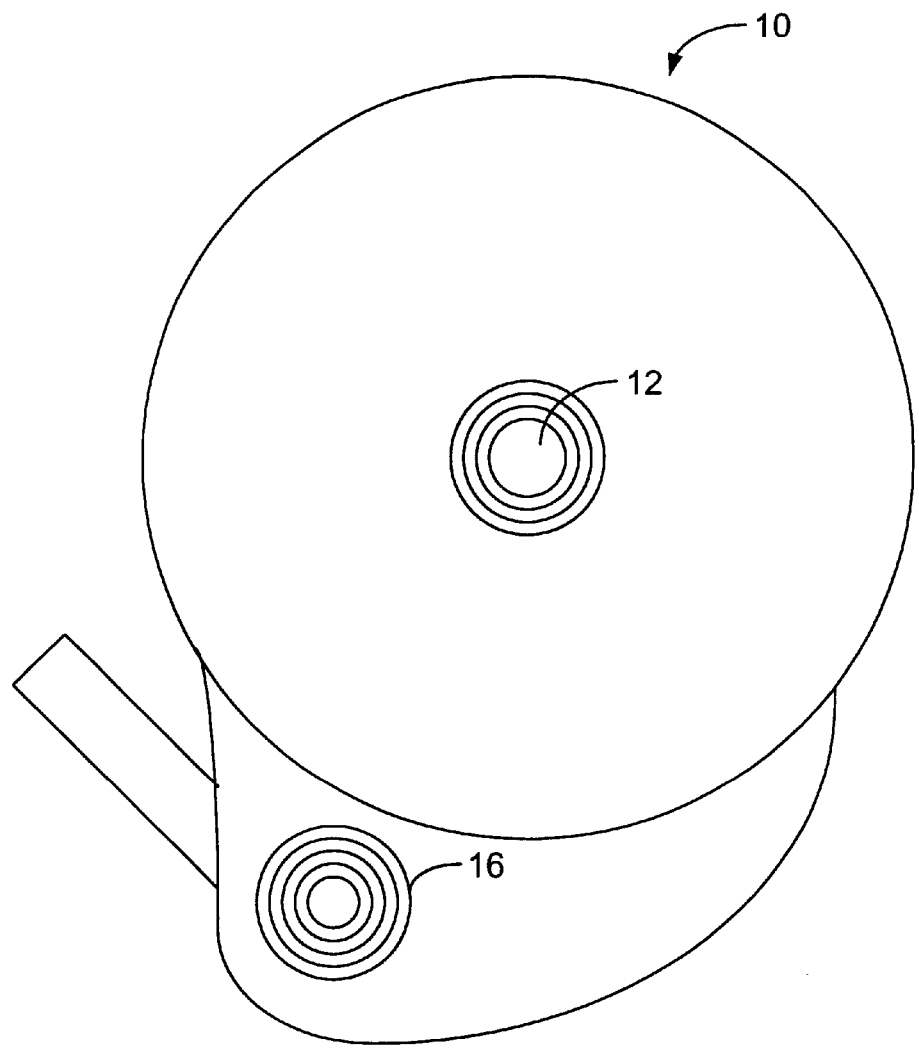
FIG. 4 is a top view of a schematic illustration of a medicament pump having a conical depression and hole of a predetermined size for limiting access to the catheter access port.
Figure 5:
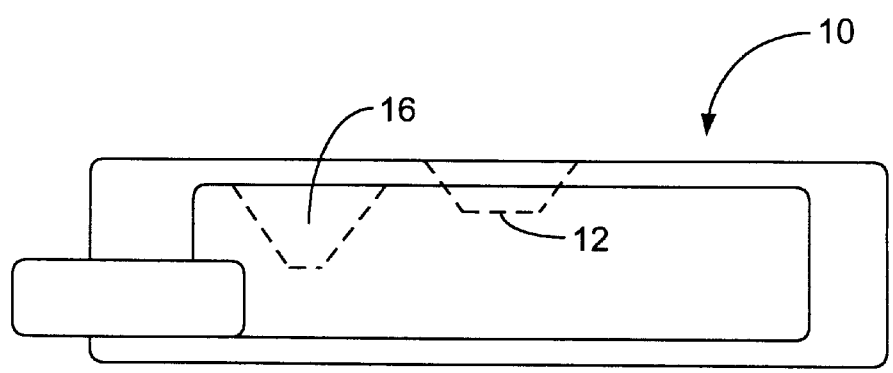
FIG. 5 is a side view of a schematic illustration of a medicament pump having a conical depression and hole of a predetermined size for limiting access to the catheter access port.
Figure 6:
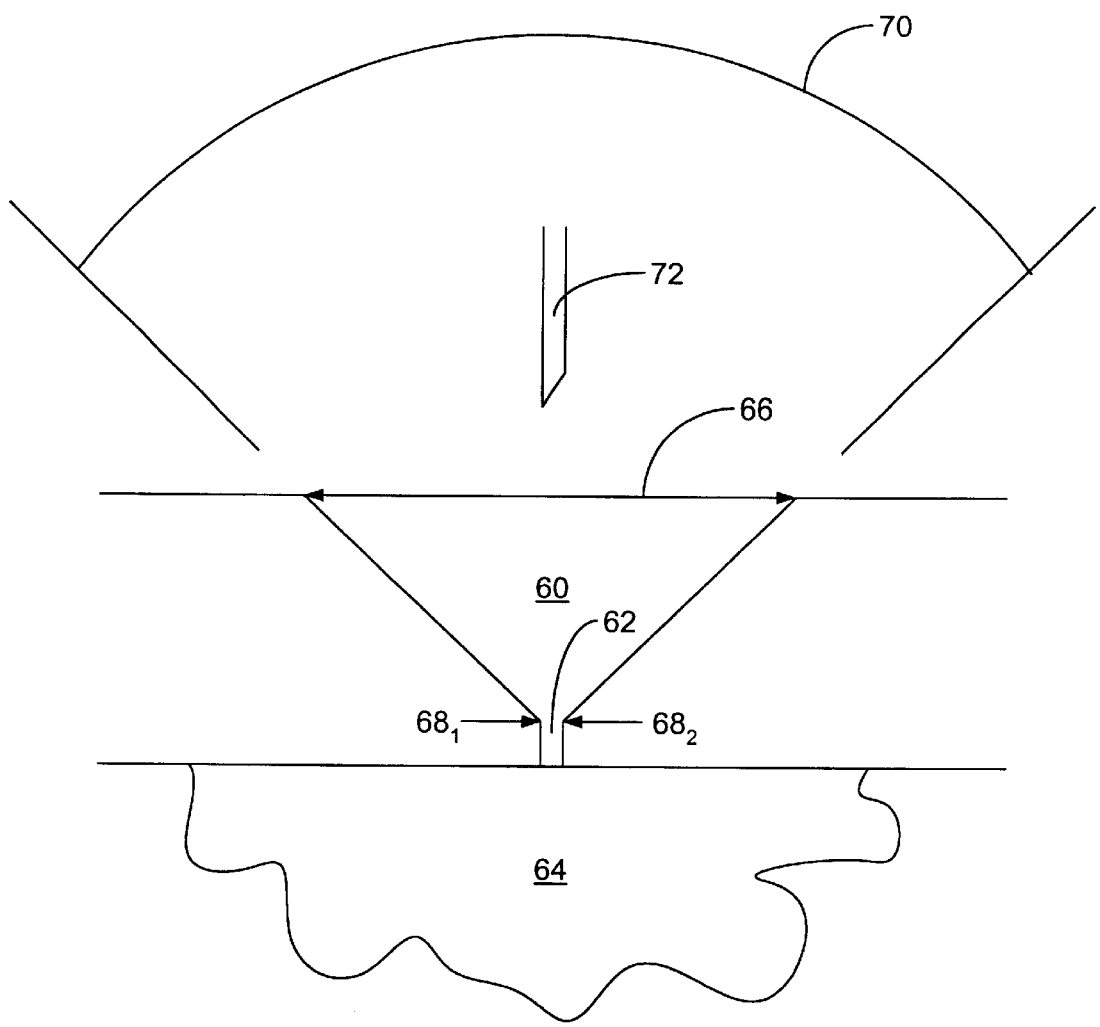
FIG. 6 is a cross sectional detailed view of the conical depression and hole of FIGS. 4 and 5.

FIGS. 4 and 5 are top and side views, respectively, of a medicament pump 10 having a catheter access port 16 including a funnel shaped conical depression and hole of a predetermined diameter, shown in detail in FIG. 6, according to the principles of this invention. Like reference numbers in FIGS. 4 and 5 correspond to like components FIG. 3. With the exception of screen 18, the discussion of the FIG. 3 applies to FIGS. 4 and 5.

FIG. 6 is a detailed sectional view of funnel shaped conical depression 60 and cylindrical hole 62 for limiting access to a particular location 64, such as a medicament pump reservoir septum. Conical depression 60 has an outer diameter, indicated by double-headed arrow 66, and an inner diameter, which is indicated by arrows $68_1$ and $68_2$ (collectively referred to as 68) and is also referred to as the diameter of hole 62. Outer diameter 66 is large enough to allow a hypodermic needle to be easily inserted within its boundaries using conventional methods such as sight and/or touch. Inner diameter 68 will typically be selected to allow only hypodermic needles smaller than or equal to a predetermined diameter to pass through hole 62 and access desired location 64. Angle 70 and the smooth finish of the surface of the conical depression 60 are such that a hypodermic needle 72 inserted within outer diameter 66 will slide toward hole 62 without bending the tip of, or otherwise damaging, hypodermic needle 72. Angle 70 is preferably between 60 and 90 degrees. Of course, other suitable angles could also be used.

In accordance with the principles of this invention, a hypodermic needle may puncture a patient's skin within outer diameter 66, but considerably off-target or misaligned from access hole 62, and move sideways guided by the surface of conical depression 60 to hole 62 without complications or discomfort to the patient. In turn, this allows a larger guiding area to be achieved without the complexity and expense associated with a plurality of holes arranged in a screen or grid for limiting access to a septum implanted within the patient's body.

The foregoing has described an apparatus and method for guiding a needle into a desired location, such as a septum implanted within a person's body, and for limiting the maximum needle size that can be used to access that location. It will be appreciated that many modifications and variations of the invention are possible, and the specific examples and descriptions herein do not limit the scope of the invention. For instance, the principles of this invention could be applied to other types of implanted ports, such as a port for a drug dosage kit having an unusually small needle to discourage accidental or intentional infusion of incorrect drugs.

I claim:

1. Apparatus for guiding a hypodermic needle to a septum in a human implantable device and for preventing access to the septum by hypodermic needles having a diameter larger than a predetermined diameter, the apparatus comprising:

a septum access port;

the septum access port including, neither more than, nor less than, one conical depression having an outer diameter, an inner diameter, and a center, the outer diameter being larger than the inner diameter; and the conical depression including, neither more than, nor less than, one hole at the center of the conical depression, the hole having a diameter substantially the same as the predetermined diameter for preventing access to the septum by hypodermic needles that have a diameter greater than the predetermined diameter.

2. The apparatus of claim 1, wherein the conical depression comprises a smooth surface for preventing damage to hypodermic needles that are inserted misaligned with the hole.

3. The apparatus of claim 1, wherein the human implantable device is a medicament pump, and the septum is a catheter access port septum.

4. Apparatus for guiding a hypodermic needle to a septum in a human implantable device and for preventing access to the septum by hypodermic needles having a diameter larger than a predetermined diameter, the apparatus comprising:

unitary conical depression means for guiding the hypodermic needle to the septum; and unitary hole means for preventing access to the septum by hypodermic needles that have a diameter greater than the predetermined diameter.

5. A method of guiding a hypodermic needle to a septum in a human implantable device and of preventing access to the septum by hypodermic needles having a diameter larger than a predetermined diameter, the method comprising the steps of:

providing, neither more than, nor less than, one conical depression to guide a hypodermic needle to the septum, the conical depression having an outer diameter, an inner diameter, and a center, the outer diameter being larger than the inner diameter; and preventing access to the septum by hypodermic needles that have a diameter greater than the predetermined diameter via, neither more than, nor less than, one hole at the center of the conical depression, the hole having a diameter substantially the same as the predetermined diameter.

6. The method of claim 5, wherein the step of providing one conical depression further comprises the step of providing a smooth conical depression surface at an angle ranging between approximately 30 degrees and approximately 45 degrees relative to an axis oriented perpendicular to an outer surface of the septum.

7. The apparatus of claim 1, wherein the inner diameter and the outer diameter define a cross-sectional angle of the conical depression, the cross-sectional angle ranging from approximately 60 degrees to approximately 90 degrees.

* * * * *